United States Patent [19]
Zahradnik et al.

[11] Patent Number: 5,716,600
[45] Date of Patent: Feb. 10, 1998

[54] STABLE STANNOUS FLUORIDE TOOTHPASTE COMPOSITIONS

[75] Inventors: Robert T. Zahradnik, Franklin, Mass.; Sima Sarker, Batesville, Ak.

[73] Assignee: Professional Dental Technologies, Inc., Batesville, Ak.

[21] Appl. No.: 557,923

[22] Filed: Nov. 14, 1995

[51] Int. Cl.$^6$ .............................. A61K 7/16; A61K 7/18; A61K 33/16
[52] U.S. Cl. .............................. 424/52; 424/40; 424/673
[58] Field of Search ................................. 424/52

[56] References Cited

U.S. PATENT DOCUMENTS

| | | |
|---|---|---|
| 3,885,028 | 5/1975 | Cella et al. . |
| 3,904,747 | 9/1975 | Cordon et al. . |
| 3,914,404 | 10/1975 | Langer . |
| 4,198,394 | 4/1980 | Faunce . |
| 4,203,966 | 5/1980 | Faunce . |
| 4,254,101 | 3/1981 | Denny, Jr. . |
| 4,292,306 | 9/1981 | Faunce . |
| 4,418,057 | 11/1983 | Groat et al. . |
| 4,469,674 | 9/1984 | Shah et al. . |
| 4,490,353 | 12/1984 | Crawford et al. . |
| 4,533,544 | 8/1985 | Groat et al. . |
| 4,540,576 | 9/1985 | Zahradnik ................. 424/52 |
| 4,568,540 | 2/1986 | Asano et al. . |
| 4,701,318 | 10/1987 | Ferlauto, Jr. et al. . |
| 4,701,319 | 10/1987 | Woo . |
| 4,702,904 | 10/1987 | Maeyama et al. . |
| 4,774,077 | 9/1988 | Ferlauto, Jr. et al. . |
| 4,902,497 | 2/1990 | Crisanti et al. . |
| 4,960,586 | 10/1990 | Suhonen . |
| 4,970,065 | 11/1990 | Suhonen . |
| 5,004,597 | 4/1991 | Majetti et al. . |
| 5,009,883 | 4/1991 | Suhonen . |
| 5,009,884 | 4/1991 | Suhonen . |
| 5,017,363 | 5/1991 | Suhonen . |
| 5,037,636 | 8/1991 | Chan . |
| 5,208,009 | 5/1993 | Gaffar et al. . |
| 5,213,790 | 5/1993 | Lukacovic et al. . |
| 5,281,411 | 1/1994 | Majeti et al. . |
| 5,338,537 | 8/1994 | White, Jr. et al. . |
| 5,403,578 | 4/1995 | Gordon . |

*Primary Examiner*—Shep K. Rose
*Attorney, Agent, or Firm*—McAulay Fisher Nissen Goldberg & Kiel, LLP

[57] ABSTRACT

The invention is a high humectant, low water, stannous fluoride containing toothpaste composition which maintains the stability and activity of the stannous fluoride over time, and methods for the preparation thereof. Stannous fluoride combined with from about 70 to about 92% humectant, and water present at less than 10% by weight, provides a stable toothpaste which avoids stannous fluoride degradation with time.

20 Claims, No Drawings

STABLE STANNOUS FLUORIDE TOOTHPASTE COMPOSITIONS

TECHNICAL FIELD

The present invention relates to high humectant—low water stannous fluoride toothpaste compositions, and methods of preparation thereof, which are stable i.e. maintain the therapeutic amounts of the stannous fluoride during storage for optimum anticaries and antigingivitis benefits.

BACKGROUND OF THE INVENTION

Stannous fluoride is well known for use in clinical dentistry with a history of therapeutic benefits dating back over forty years. However, until recently, its popularity has been limited by its instability in aqueous solutions. The instability of stannous fluoride in water is primarily due to the reactivity of the stannous ion ($Sn^{2+}$). Tin readily hydrolyses above pH 4, resulting in precipitation from solution, with a consequent loss of the therapeutic properties.

The first stannous fluoride containing dentifrice formulation, known as Crest® with Fluoristan™ (stannous fluoride), was manufactured by Procter & Gamble. This dentifrice demonstrated significant anticaries benefits. However, much of the stannous and fluoride ion concentration gradually reacts with a loss of these beneficial properties. The original aqueous stannous fluoride formulation has been reformulated with sodium fluoride substituted for the stannous fluoride because of the instability of the stannous ions in the water-based formulation.

One approach to overcome the stability problem with stannous fluoride was to form a gel by dissolving stannous fluoride in an anhydrous material such as glycerin and eliminating mineral abrasives. U.S. Pat. Nos. 4,418,057 and 4,533,544 describe methods where stannous fluoride is formulated as a non-aqueous gel mixture including anhydrous glycerin and hydroxyethyl cellulose gelling agent. Total exclusion of moisture during manufacture and storage is required to protect the stannous ion. The methods are specifically for manufacture of a stannous fluoride dental gel, and not for dentifrice compositions containing abrasives. Although generally stable, such compositions do not provide the cleaning and aesthetic benefits associated with conventional dentifrices. Furthermore, these gels are typically of thin consistency, because the binders needed to thicken the formulation require hydration, which would reduce the activity of the stannous fluoride ions.

Recently, multiple benefit dentifrice formulations have been prepared that are capable of addressing more than an anticaries need. These include antitartar benefits, control of dentinal hypersensitivity and antigingivitis efficacy. This has renewed interest in stannous fluoride. In fact, several studies since 1984 have shown that stannous fluoride has clinical antigingivitis activity when used in concentrations around 0.4 weight percent, as either a mouthrinse or a dentifrice formulation. The clinical effects of stannous fluoride on gingivitis are generally accepted as being related to its antimicrobial actions, which include inhibition of bacterial adhesion, growth and carbohydrate metabolism. However, to use stannous fluoride in toothpaste formulations, it is necessary to solve the stability problem.

Attempts have been made to stabilize stannous fluoride for prolonged time periods in aqueous dentifrice formulations by employing chelating (metal binding) agents which bind stannous fluoride, and by using stannous reservoirs of sparingly soluble stannous salts that act both as a supply of stannous ions and as an antioxidant. For example, U.S. Pat. No. 5,004,597 describes compositions containing stannous fluoride and stannous gluconate salt to provide a stannous reservoir. Such approaches can over-stabilize the product, making the stannous fluoride logically inactive in the mouth. In addition, this requires the use of excessive levels of stannous (about 3.5 times the amount contributed by the active agent, stannous fluoride).

U.S. Pat. No. 4,254,101 describes compositions containing high levels of a humectant, along with silica abrasive, a carboxyvinyl polymer, water, and fluoride compounds as optional ingredients. A variety of fluoride compounds including stannous fluoride are described as suitable optional ingredients. However, no suggestion is made concerning stability and it is likely that stability was not considered important to the dentifrice disclosed, particularly since none of the examples used stannous fluoride.

U.S. Pat. Nos. 4,960,586 and 4,961,924 describe oral compositions containing stannous fluoride and include an alkyl vinyl ether and maleic anhydride acid copolymer as a stabilizing agent. However, such a chemically stabilized stannous ion has very limited bioavailability as determined through antibacterial testing.

SUMMARY AND OBJECTS OF THE INVENTION

It is an object of the present invention to provide a toothpaste composition which utilizes stannous fluoride in a stable form, in combination with water, mineral abrasives, thickeners and other desirable ingredients, but without utilizing stabilizers, chelants or stannous reservoirs.

It is a further object of the present invention to provide compositions containing stannous fluoride, which are useful in retarding the development of plaque/gingivitis.

Those and other objects of the present invention are achieved by a low water base toothpaste composition comprising:

(a) a safe and effective amount of stannous fluoride, (b) a humectant, present at from about 70 to about 92%, and (c) between 1 and 10 weight percent water, the composition having a pH of from about 2.5 to 5.0.

Other ingredients which may be used include thickeners, mineral abrasives, foaming agents, flavor agents, etc.

The method for formulating the low water base stannous fluoride toothpaste comprises:

(a) dispersing stannous fluoride in a heated portion of a non-aqueous humectant;

(b) adding a thickener directly to the mixture of step (a), or dispersing the thickener in a second portion of hot humectant and then adding the thickener/humectant to the mixture of step (a), to form mixture (b);

(c) placing an abrasive in a third portion of the humectant and then adding the abrasive/humectant to mixture (b), or adding the abrasive directly into the mixture (b), to form a mixture (c); and (d) adding water in an amount comprising less than 10% of the toothpaste to mixture (c).

If other optional ingredients are needed, the method further comprises (e), adding the optional ingredients to the water before it is added to mixture (c).

The order of ingredient addition is necessary to protect the stannous fluoride from degradation during manufacture to assure long-term stability. In addition, the temperature, mixing rate, pressure/vacuum should be sufficiently controlled to limit moisture and air absorption during manufacture. However, once formulated, the toothpaste of the invention exhibits excellent stability and bioavailability of stannous fluoride when subject to aging tests.

DETAILED DESCRIPTION OF THE INVENTION

The toothpaste composition of the present invention comprises the following essential ingredients: stannous fluoride as the active ingredient, a humectant, from 1 to 10% water, and preferably a dental abrasive and thickeners to achieve a consistency preferred by toothpaste users. Other optional ingredients such as emulsifying agents, favorants, food dyes, and sweeteners can be added to the toothpaste composition, because the toothpaste, as distinguished from gels, contains water without detrimentally affecting the stannous fluoride stability achieved with the invention.

The term "stable" is defined to mean that the stannous and fluoride ion concentrations, after three months storage at thirty-eight degrees Celsius or two years at room temperature, remain at sufficient high levels to maintain biological activity.

The term "biologically active" is used to indicate the extent (rate and amount) to which stannous fluoride reaches its site of action. Biological activity can be estimated in vitro through standard laboratory tests for fluoride uptake into human enamel samples and for antibacterial activity, or clinically through human studies for anticaries and antigingivitis benefits.

Stannous fluoride is the first essential component of the present toothpaste compositions. This material is present in the compositions at a level of from about 0.05 to about 1.6 weight percent, most preferably at about 0.45 weight percent. All percentages and ratios used herein are by weight of the total composition unless otherwise specified. The stannous fluoride is effectively stabilized in the present compositions by maintaining low water ("low" meaning less than 10%) and a pH at or below 5.0.

The composition contains from about 1 to about 10%, more preferably about 1 to 8% water. This amount of water includes the free water which is added plus that which is introduced with other optional ingredients such as aqueous sorbitol or sodium lauryl sulfate. The pH of the toothpaste composition is below 5 so as to provide optimal stability of the stannous-fluoride ion complex in the aqueous phase. Preferably, the pH is between from about 2.5 to about 5.0, more preferably from about 3.0 to about 4.2, most preferably about 3.5.

The humectant is an essential ingredient, and this must be present in the toothpaste at a level of from about 70 to about 92%. The preferred humectant is anhydrous glycerin, though sorbitol, as a 70 percent solution, may be substituted for up to 10 percent of the glycerin. Other suitable humectants include any of the edible polyhydric alcohols, such as polyethylene glycol, provided they are used in a water-free form.

An abrasive polishing material is contemplated for use in the present invention. This can be any material which does not excessively abrade dentin and which does not provide calcium ions which may precipitate with, for example, the fluoride ion provided from stannous fluoride. Acceptable abrasives include, for example, silicas, including gels and precipitates thereof, insoluble sodium polymetaphosphate, beta-phase calcium pyrophosphate, and hydrated alumina.

Silica dental abrasives can provide exceptional dental cleaning and polishing performance without unduly abrading tooth enamel or dentin. Silica abrasives are generally compatible with sources of soluble fluoride and are preferred for use herein. However, stannous fluoride may interact to a small degree with hydrated silica at pH's of less than 5. For this reason, it may be preferred to protect the silica to block sites of interaction with stannous fluoride before inclusion in the inventive toothpaste, and this will be discussed further below.

The abrasive polishing materials useful herein generally have an average particle size ranging from about 0.1 to about 30 microns, preferably about 5 to 15 microns. The abrasive is present at from about 5% to about 25%, preferably from about 7 to about 15% of the toothpaste composition.

In preparing a toothpaste, it is usually necessary to add a thickener, sometimes referred to as a binder, to provide a desirable consistency. A toothpaste containing high levels of humectant and low water content presents a particular thickening problem. Many conventional thickeners such as carboxymethyl cellulose do not function well in low hydration compositions. Furthermore, cellulose gums react with stannous fluoride and can significantly reduce the available stannous ion concentration in dentifrice formulations. However, hydroxyethyl cellulose and carboxyvinyl polymers function well in the inventive compositions. Those particularly useful in the toothpastes described herein are carboxyvinyl polymers made by B. F. Goodrich and designated by the trade names "Carbopol 934", "Carbopol 940", "Carbopol 941", "Carbopol 974" and "Carbopol 980". The thickener is present in the proposed composition at a level of from about 0.05% to about 3.0%, preferably from about 0.4 % to 1.5%.

For optimal rheological properties and dispersibility, at least one secondary thickener/binder should be used in addition to the thickener. Among the preferred secondary thickening agents are xanthan gum, carrageenan, colloidal magnesium aluminum silicate and finely divided silica. Silica thickeners are particularly useful and are preferred in the present composition. These secondary thickeners, if used, should be present as part of the total thickener added, and comprise about 0.5 to about 2.0% more preferably about 0.6 to about 1.4% of the composition.

Flavoring agents can also be added. Suitable flavoring agents include, but are not limited to, oil of wintergreen, oil of peppermint, oil of spearmint, oil of sassafras, and oil of clove. Sweetening agents can also be used, including aspartame, acesulfame, saccharin, dextrose, levulose and sodium cyclamate. Flavoring and sweetening agents are generally used in toothpastes at levels of from about 0.005% to about 2% by weight. Coolants and opacifiers, such as titanium dioxide, of course, can be included in the inventive composition.

The toothpaste composition can also contain emulsifying agents, preferably those which are reasonably stable and foam throughout a wide pH range, including non-soap anionic, nonionic, cationic, zwitterionic and amphoteric organic synthetic emulsifiers, sodium lauryl sulfate is an exemplary emulsifying agent.

Other optional ingredients include those with therapeutic benefit. These include, but are not limited to, antitartar agents, dentin desensitizers such as potassium nitrite, and antimicrobials, such as quaternary ammonium salts, bis-bisquanide salts, nonionic antimicrobial salts and essential oils.

Toothpaste compositions of the present invention can be made using methods which are reasonably common to the oral products area. However, the inventive method requires a particular order of addition of the individual ingredients, and precautions to avoid excess moisture during manufacture. This is important for successful preparation of the stable toothpaste of the invention. In addition, the manufacturing procedure preferably involves various combinations of heating, cooling and mixing sequences to produce an optimal stable stannous fluoride toothpaste composition, with desirable rheological properties and specific density limits. Control of air content can assure that specific density limits are consistently met.

The preferred ingredients and method steps of the invention follow and include:

(a) dissolving stannous fluoride in anhydrous glycerin, heated to a temperature in the range of from about 95° C. to about 180° C., preferably from about 100° C. to about 110° C., in a mixing vessel which is preferably jacketed and which has provision for heating and/or cooling the mixture, as well as for internal vacuum/pressure control;

(b) reducing the mixture temperature to from about 80° C. to about 100° C.;

(c) adding a carboxyvinyl polymer, through a screen to minimize lumping, preferably using a high speed disperser or high shear mixer-emulsifier (to minimize air entrapment, this is preferably done with the mixture under vacuum);

(d) adding a secondary thickener after the temperature in the mixing vessel is allowed to reach about 50° C. to about 80° C., with high shear mixing and deaeration employed, until a homogeneous composition is formed;

(e) reducing the temperature further to about 25° C. to about 40° C., and then adding an abrasive directly with agitation (low shear conditions are preferred at this stage of manufacture);

(f) preparing an admixture of an emulsifier in an amount of water being less than 10%, with other optional ingredients such as flavoring agents, sweeteners and food dyes;

(g) adding the admixture slowly using the minimum agitation needed for homogeneous blending. Alternatively, the emulsifier may be mixed with a polyol, heated and deaerated before blending with the other toothpaste components.

An alternative method would involve the preparation of four separate admixtures in different vessels, and then blending the admixtures in the prescribed sequence, as described below. The steps include:

(a) dispersing the needed amount of thickener in about 50% to about 60% of the humectant, contained in a main mixing vessel, the humectant heated to from about 50° C. to about 100° C., preferably using high shear agitation to insure complete dispersion;

(b) adding the abrasive to about 25% to about 35% of the humectant in a separate vessel maintained at room temperature and mixing to form an abrasive slurry, which is then added to mixture (a) above, after the mixture temperature has been allowed to cool below about 40° C.;

(c) heating about 6% to about 15% of the humectant to, preferably, about 100° C. to about 110° C. in a separate vessel, and then adding the needed amount of stannous fluoride and mixing until the stannous fluoride is dissolved, then cooling to about room temperature and adding this to the main mixing vessel containing (a) and (b) above, which also has been allowed to cool to about room temperature; and (d) preparing a mixture of the secondary thickener in the formula amount of water with optional ingredients such as flavoring agents, sweeteners and food dyes, this mixture then added slowly to the main mixing vessel, using the minimum agitation needed for homogeneous blending.

Alternatively, the optional ingredients may be dissolved in the formula amount of water and added directly to the main vessel, and the secondary thickener may be mixed separately with a non-aqueous solvent and heated and deaerated before blending with the other toothpaste admixtures.

The compositions of this invention are preferably prepared under conditions which protect the stannous ion from oxidation and hydrolysis, such as by carrying out the blending process under vacuum or in an inert atmosphere.

If silica is used as the abrasive, an additional step may be used to prevent deterioration of stannous fluoride levels over prolonged periods of storage. Stannous fluoride may interact to some extent with silica, and about 5% to 10% of the total amount of stannous and fluoride ion may be inactivated. This is avoided by pretreating the silica by mixing with either an aqueous solution containing a known stannous chelate such as stannous gluconate at a level of from about 0.1% to about 11%, preferably from about 2% to about 4% or with an aqueous etchant such as hydrofluoric acid.

Stannous gluconate is the preferred chelating agent and may be provided in a pretreatment solution as the chelate or as separate soluble stannous and gluconate salts, with the chelate formed in situ. Such salts include stannous chloride and sodium gluconate. Use of an aqueous etchant, such as hydrofluoric acid, involves treating the silica with an acid solution at a level of about 0.1 to about 6.0% weight. In either case, the pretreated silica is washed with water to remove excess etchant or chelating agent and then dried before use in the toothpaste composition.

Toothpaste compositions of the present invention are used in a conventional manner. The toothpaste compositions or slurries thereof are brushed onto dental surfaces in amounts from about 0.2 gram to about 2 grams, and subsequently rinsed away. During use of the toothpaste herein, pastes or slurries generally contact dental surfaces for from about 15 seconds to about 60 seconds.

The following examples further describe and demonstrate preferred embodiments within the scope of the present invention. The examples are given solely for illustration and are not to be construed as limitations of this invention as many variations are possible without departing from the scope of the invention.

TABLE I

EXAMPLES I–IV

| Components | Weight % | | | |
|---|---|---|---|---|
|  | I | II | III | IV |
| Water, Purified | 5.000 | 2.500 | 2.500 | 3.000 |
| Sorbitol (70% solution) | — | 10.000 | — | — |
| Glycerin | 80.126 | 72.676 | 86.226 | 0.896 |
| Polyethylene Glycol | — | — | — | 2.000 |
| Titanium Dioxide | — | — | — | 0.500 |
| Silica Abrasive | 11.000 | 11.000 | 7.000 | 9.000 |
| Carboxyvinyl Polymer | — | 0.800 | 0.800 | 0.750 |
| Hydroxyethyl Cellulose | 0.600 | — | — | — |
| Xanthan Gum | 0.600 | 0.600 | 0.500 | 0.400 |
| Silica Thickener | — | — | 0.500 | 1.000 |
| Sodium Lauryl Sulfate | 1.250 | 1.000 | 0.750 | 0.750 |
| Stannous Fluoride | 0.454 | 0.454 | 0.454 | 0.454 |
| Sodium Saccharin | 0.200 | 0.200 | 0.250 | 0.250 |
| Peppermint | 0.750 | 0.750 | 1.000 | 1.000 |
| FD&C Blue #1 (1% Solution) | 0.020 | 0.020 | 0.020 | — |
| pH | 4.2 | 3.5 | 3.5 | 3.5 |

TABLE II

| Compositions | Theoretical, ppm | | 12 month aging, ppm | | | | Bioavailable |
|---|---|---|---|---|---|---|---|
| | SN | F | SN | % Theo | F | % Theo | |
| Crest Gum Care | 11,284 | 1,100 | 4,400 | (39%) | 800 | (73%) | Yes |
| Oral-B Tooth/Gum Care | 3,000 | 1,000 | 2,740 | (91%) | 620 | (62%) | No |
| Inventive Toothpaste | 3,300 | 1,100 | 3,100 | (94%) | 935 | (85%) | Yes |

As shown in Table II, the present invention provides long term stability of stannous fluoride with 12 month aging, without using stabilizers (Oral-B) or stannous reservoirs (Crest), and in fact is superior to either of the two for delivering stannous fluoride.

What is claimed is:

1. A stable stannous fluoride toothpaste consisting essentially of an effective amount of stannous fluoride, an anhydrous humectant in an amount of from about 70 to 92% by weight, water from about 1% to about 8%, an abrasive, and a thickener, the composition having a pH of from about 2.5 to 5.0, the toothpaste produced by a process having the steps of:

(a) dispersing the effective amount of stannous fluoride in a heated portion of the anhydrous humectant to form a mixture a;

(b) dispersing the thickener directly in mixture a, or, dispersing the thickener in a second portion of hot humectant and then adding this mixture to mixture a, to form a mixture b;

(c) dispersing the abrasive in a portion of the anhydrous humectant at room temperature and adding the dispersion to mixture b to form a mixture c or adding the abrasive directly to the mixture b to form mixture c; and (d) slowly adding the amount of water to mixture c.

2. The toothpaste composition according to claim 1 wherein the amount of stannous fluoride is from about 0.05% to about 1.6%.

3. The toothpaste composition according to claim 1 where the abrasive is silica.

4. The toothpaste of claim 1 wherein the thickener is from the group consisting of carboxyvinyl polymer, hydroxyethyl cellulose, xanthan gum, carrageenan, colloidal magnesium aluminum silicate, finely divided silica, and combinations thereof.

5. The toothpaste composition of claim 1 wherein the amount of stannous fluoride is about 0.45%.

6. The toothpaste composition of claim 1 wherein the pH is from about 3.0 to about 4.2.

7. The toothpaste composition of claim 1 wherein the humectant comprises a mixture of humectants having up to 10% glycerin.

8. The toothpaste composition of claim 1 wherein the humectant is from the group consisting of anhydrous glycerin, sorbitol, non-aqueous polyhydric alcohols and mixtures thereof.

9. The toothpaste composition of claim 1 wherein the abrasive is present at from about 5% to about 25%.

10. The toothpaste composition of claim 1 wherein the abrasive is present at from about 7% to about 15%.

11. The toothpaste composition of claim 1 wherein the thickener is present at from about 0.05% to about 3.0%.

12. The toothpaste composition of claim 1 wherein the thickener is present at from about 0.4 to about 1.5%.

13. The toothpaste composition of claim 1 further comprising optional ingredients added to the amount of water, prior to adding water to mixture c, the optional ingredients selected from the group consisting of flavoring agents, emulsifying agents, antitartar agents, dentin desensitizers and antimicrobials.

14. A toothpaste composition consisting essential of:

stannous fluoride at from about 0.005 to about 1.6%;

a humectant at from abut 70 to about 92%;

water at from about 1% to about 8%;

an abrasive at from about 5% to about 25%;

a thickener at about 0.05 to about 3.0%; and the composition having a pH of from about 2.5 to 5.0.

15. The toothpaste composition of claim 14 wherein stannous fluoride is present at 0.45%, the humectant is glycerine present at about 72 to 86%, water is present at from about 2.5 to 5.5%, the abrasive is silica present at from 9 to 11%, the thickener is present at from about 1.2 to about 2.2%, the composition having a pH of about 3.5 to about 4.2.

16. The composition of claim 14 further comprising an emulsifier at from about 0.75 to about 1.25%.

17. The composition of claim 14 further comprising a sweetener present at from about 0.2% to about 0.25%.

18. The composition of claim 14 further comprising a flavoring agent present at about 0.75 to about 1.0%.

19. A method of manufacturing a stable stannous fluoride toothpaste consisting essentially of:

(a) dispersing an effective amount of stannous fluoride in a heated portion of an anhydrous humectant to form a mixture a;

(b) dispersing a thickener directly in mixture a or dispersing the thickener in a second portion of hot anhydrous humectant and then adding this dispersion to mixture a, to form a mixture b;

(c) dispersing an abrasive in a portion of the anhydrous humectant at room temperature and adding the abrasive dispersion to mixture b to form mixture c, or adding the abrasive directly to the mixture b to form mixture c; and (d) slowly adding an amount of water, not to exceed 8% of the composition to mixture c.

20. The method of claim 19 further comprising adding optional ingredients to the amount of water, prior to adding the water to mixture (c).

* * * * *